(12) United States Patent
Weber et al.

(10) Patent No.: US 6,180,831 B1
(45) Date of Patent: Jan. 30, 2001

(54) METHOD OF PRODUCING β-HYDROXYALDEHYDES

(75) Inventors: Robert Weber; Wilhelm Keim, both of Aachen; Bernd Jaeger, Darmstadt; Thomas Haas, Frankfurt; Rudolf Vanheertum, Kahl, all of (DE)

(73) Assignee: Degussa-Huls AG, Frankfurt am Main (DE)

( * ) Notice: Under 35 U.S.C. 154(b), the term of this patent shall be extended for 0 days.

(21) Appl. No.: 09/438,376

(22) Filed: Nov. 12, 1999

(30) Foreign Application Priority Data

Nov. 12, 1998 (DE) ................................ 198 52 104

(51) Int. Cl.⁷ .................................................. C07C 45/49
(52) U.S. Cl. ........................................... 568/454; 568/483
(58) Field of Search ................... 568/442, 451, 568/483, 454

(56) References Cited

U.S. PATENT DOCUMENTS 5,256,827 * 10/1993 Slaugh et al. ..................... 568/454
5,304,691   4/1994 Arhancet et al. .
5,723,389 * 3/1998 Slaugh et al. ..................... 468/862
5,767,321 * 6/1998 Billig et al. ....................... 568/454

FOREIGN PATENT DOCUMENTS 0073961   3/1983 (EP) .
0455261  11/1991 (EP) .
96/10552  4/1996 (WO) .

OTHER PUBLICATIONS

Abu–Gnim et al., Phosphine Oxides as Ligands in the Hydroformylation Reaction, J. Organomet. Chem., vol. 516 (1–2) 1996, pp. 235–243.

* cited by examiner

Primary Examiner—Jean F Vollano
(74) Attorney, Agent, or Firm—Pillsbury Madison & Sutro LLP

(57) ABSTRACT

β-Hydroxyaldehydes are produced by a method in which 1,2-oxiranes are reacted with carbon monoxide and hydrogen in the presence of transitional metal compounds which are modified with phosphorus-oxygen ligands or nitrogen-oxygen ligands and which act as a catalyst.

16 Claims, No Drawings

METHOD OF PRODUCING β-HYDROXYALDEHYDES

CROSS-REFERENCE TO RELATED APPLICATION

This application is based on German Application DE 198 52 104.9, filed Nov. 12, 1998, which disclosure is incorporated herein by reference.

FIELD OF THE INVENTION

The invention relates to a method of producing β-hydroxyaldehydes.

BACKGROUND OF THE INVENTION

β-Hydroxyaldehydes are significant as starting compounds for the production of compounds such as, e.g., dicarboxylic acids and their derivatives. Furthermore, diols such as, e.g., 1,3-propane diols, can be produced by the hydrogenation of β-hydroxyaldehydes. 1,3-Propane diols can be used as monomeric structural units in the production of polyesters or polyurethanes, as starting materials for the synthesis of cyclic compounds as well as for a number of other substances.

It is known that β-hydroxyaldehydes can be produced by reacting 1,2-oxiranes with carbon monoxide and hydrogen in the presence of catalysts.

U.S. Pat. No. 3,463,819 describes a method for the production of β-hydroxypropionaldehyde and 1,3-propanediol in which, inter alia, ethylene oxide in the presence of toluene as well as in the presence of diethylether/benzene, 1,2-bis(diphenylphosphino)ethanedicobalt hexacarbonyl, carbon monoxide and hydrogen are reacted with each other.

U.S. Pat. No. 3,456,017 describes a method for the production of propanediol and β-hydroxypropionaldehyde in which ethylene oxide, a tertiary phosphino-modified cobalt carbonyl catalyst, carbon monoxide and hydrogen are reacted with each other.

U.S. Pat. No. 5,256,827 describes the hydroformylation of ethylene oxide in the presence of oxidized, tertiary phosphine-complexed carbonyl catalysts.

The known methods have the disadvantage that a very great amount of catalyst relative to the amount of ethylene oxide must be used, Furthermore, reaction promoters must be added.

The invention has the object of developing a method for the production of β-hydroxyaldehydes which does not have these disadvantages.

SUMMARY OF THE INVENTION

The invention provides a method of producing β-hydroxyaldehydes in which 1,2-oxiranes are reacted with carbon monoxide and hydrogen in the presence of transitional metal compounds which are modified with phosphorus-oxygen ligands or nitrogen-oxygen ligands and which act as catalyst.

According to the invention, 1,2-oxiranes (epoxides) are hydroformylated with carbon monoxide and hydrogen in the presence of a cobalt-carbonyl catalyst modified with phosphorus-oxygen chelate ligands or nitrogen-oxygen chelate ligands. The reaction products are essentially β-hydroxyaldehydes (and their oligomers) and, in small amounts, the corresponding 1,3-diols. When the term "β-hydroxyaldehydes" is used below it signifies the monomers as well as the dimers such as, e.g., 2-(2-hydroxyethyl)-4-hydroxy-1,3-dioxane in the case of the hydroformylation of ethylene oxide as well as trimers and higher oligomers of the corresponding β-hydroxyaldehydes.

Oxiranes containing 2 to 30 carbon atoms can be used, for example, as the oxiranes. Epoxides having an oxygen bridge in the 1,2 position are preferably used.

Saturated hydrocarbons with vicinal epoxides with up to 10 carbon atoms can be used as oxiranes in the method of the invention. These compounds, also named epoxyalkanes, can have cyclic or acyclic, long-chain or branched-chain structures.

Acyclic epoxides can be those epoxides in which the carbon atoms of the epoxy unit are not a component of a carbocyclic ring. Such compounds are, e.g., ethylene oxide, propylene oxide, isobutylene oxide, 1,2-epoxypentane, 1,2-epoxy-4-methylpentane, 1,2-epoxyoctane, 3-cyclohexyl-1,2-epoxypropane, 3,4-epoxynonane, 1,2-epoxy-2,2,4-trimethylhexane and 1,2-epoxydecane.

Cyclic epoxides can be those epoxides in which the carbon atoms of the epoxy unit are part of a carbocyclic ring. Such epoxycycloalkanes can be, e.g.: cyclohexene oxide, cyclopentene oxide, cyclooctane oxide, 1,2-epoxy-4-methylcyclohexane, 4,5-dimethyl-1,2-epoxycyclohexane, 2,3-epoxy-decahydronaphthalene and 1,2-epoxy-4-propylcyclohexane.

In general, the use of acyclic epoxides is preferred. In particular, acyclic epoxides with a carbon-atom number up to 6 carbon atoms in which the epoxy group is terminal, such as, for example an acyclic 1,2-epoxyalkane, can be used. Of these compounds, ethylene oxide as well as propylene oxide are particularly preferred.

Cobalt-carbonyl catalysts modified with phosphorus-oxygen chelate ligands can be used as catalysts in the method of the invention.

For example, phosphine-phosphinic oxides can be considered as chelate ligands. Preferred phosphine-phosphinic oxides which correspond to formula (I) are preferred.

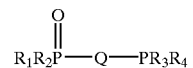

(I)

in which $R_1$, $R_2$, $R_3$, $R_4$ are the same or different and represent an alkyl-, cycloalkyl- or aryl group of up to 30 carbon atoms, preferably up to 12 carbon atoms, or —$CH_2OH$, and Q represents an alkylidene bridge having 1–20 carbon atoms, preferably having 1–10 carbon atoms, a heteroatom such as, e.g., oxygen, or alkylidene compounds containing nitrogen.

Especially preferred substances corresponding to formula (I) are 1,2-bis(diphenylphosphino)methane monoxide (dppmO) and 1,2-bis(diphenylphosphino)ethane monoxide (dppeO).

These compounds are known from U.S. Pat. No. 4,429,161 and U.S. Pat. No. 3,426,021, as well as from N. A. Bondarenko, Synthesis 1991, 125.

The phosphinic oxides used in accordance with the invention are defined compounds characterized by a ratio of oxygen to phosphorus of equal to or greater than 0.5.

In a preferred embodiment the ratio of oxygen to phosphorus can be 0.5 to 2.0.

Furthermore, for example, aliphatic and aromatic phosphino carboxylic acids and their esters can be considered as ligands.

These compounds are known from K. Issleib and G. Thomas in Chem. Ber., 1960, (93), 803–808. They can be produced according to O. Stelzer et al., J. Organomet. Chem. 1996, 522, 69–76, as well as according to Rauchfuss, Inorg. Synth., 21, 1982.

The preferred ligands are represented by formulas (II) and (III)

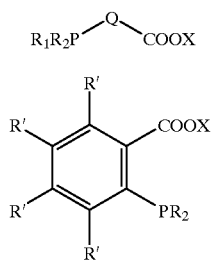

in which
R₁, R₂ can be the same or different and represent an alkyl-, cycloalkyl- or aryl group of up to 30 carbon atoms, preferably up to 12 carbon atoms, or —CH₂OH,
R' represents hydrogen or an alkyl- or cycloalkyl group of up to 30 carbon atoms, preferably up to 12 carbon atoms,
Q represents an alkylidene bridge having 1–20 carbon atoms, preferably having 1–10 carbon atoms,
X represents hydrogen in the case of phosphino carboxylic acids and an alkyl-, cycloalkyl- or aryl group in the case of the esters.

Diphenylphosphino acetic acid and diphenylphosphino methyl acetate are especially preferred substances according to formula (II).

o-Diphenylphosphino benzoic acid and o-diphenylphosphino methyl benzoate are especially preferred substances according to formula (III).

Moreover, cobalt-carbonyl compounds modified with nitrogen-oxygen chelate ligands can be used in the method of the invention.

For example, di-N-substituted amino carboxylic acids as well as their esters can be used.

Ligands which correspond to formula (IV), set forth below, are preferred,

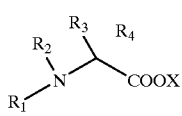

in which:
R₁, R₂, R₃, R₄ each represent hydrogen or an alkyl-, cycloalkyl or aryl group of up to 30 carbon atoms, preferably up to 12 carbon atoms, which can additionally carry other functionalities such as hydroxyl-, amino- or halogen groups.
R₁ and R₂ as well as R₃ and R₄ can also be included in a common cycloalkyl group with up to 20 carbon atoms, preferably 4–7 carbon atoms.
X represents hydrogen in the case of amino carboxylic acids, and an alkyl-, cycloalkyl or aryl group in the case of esters.

Especially preferred substances corresponding to formula IV are N,N-dimethyl glycine and its ethyl esters.

When R₃≠R₄, the compounds according to formula IV can be produced in the form of the pure enantiomers in order to transfer chiral information to corresponding chiral epoxides in this manner.

Furthermore, substances are preferred which correspond to formula V

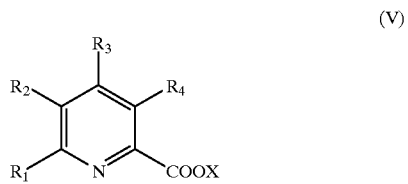

in which
R₁, R₂, R₃, R₄ each represent hydrogen or an alkyl-, cycloalkyl or aryl group of up to 30 carbon atoms, preferably up to 12 carbon atoms, which can additionally carry other functionalities such as hydroxyl-, amino- or halogen groups.
R₁ and R₂ as well as R₃ and R₄ can also represent an aromatic or cycloalkyl group with up to 20 carbon atoms, preferably with 4–7 carbon atoms.
X represents hydrogen in the case of amino carboxylic acids, and an alkyl-, cycloalkyl or aryl group in the case of the esters.

Especially preferred substances corresponding to formula V are picolinic acids (pyridine-2-carboxylic acid) and their ethyl esters.

For example, salts with organic or inorganic anions can be used as cobalt compounds. Carbon monoxide complexes of cobalt are preferred. Dicobalt octacarbonyl is an especially preferred cobalt compound.

There are a number of methods for the production of cobalt carbonyl catalysts modified with phosphorus-oxygen ligands or P—O and N—O chelate ligands. It is possible, for example, to heat cobalt complexes such as, e.g., dicobalt octacarbonyl and a suitable ligand together. The ligand will replace a corresponding number of carbonyl functions and yield the desired catalytic precursor in this manner. It should be taken into consideration that a coordination of the ligands is possible via the phosphorus atom or nitrogen atom as well as via the oxygen atom. If this reaction is carried out in a suitable solvent it is possible to obtain the complex in crystalline form, by cooling.

A further possibility is in situ production. For this, cobalt compounds such as, e.g., cobalt octacarbonyl and a suitable ligand are added successively into the reaction solution. The catalytically active complex forms under the selected reaction conditions.

The ratio of ligand to cobalt is preferably between 0.1:1 and 5:1.

For example, 0.5 to 0.0001 mole catalyst can be used relative to 1 mole epoxide. This amount is preferably approximately 0.2 to 0.002 mole.

The hydroformylation method of the invention can be carried out at temperatures in a range of 30°–150° C. and pressures between 50 and 300 bar. The method is preferably carried out at 70°–120° C. and pressures between 90 and 200 bar.

The method of the invention comprises the reaction of an epoxide in the presence of a catalyst with hydrogen and carbon monoxide. A ratio of hydrogen to carbon monoxide between 6:1 and 1:1 is preferred.

Compounds which are liquid at the given temperatures and pressures and inert to the reactants and catalysts can be used as solvent. These are, for example, aliphatic and aromatic hydrocarbons, chlorine-containing aliphatic and aromatic hydrocarbons as well as linear and cyclic ethers. Preferred solvents are benzene, toluene, diethylether, MTBE and tetrahydrofuran.

The method of the invention has the following advantages:

The hydroformylation of 1,2-epoxides can be carried out in such a manner that the β-hydroxyaldehydes are formed selectively to a high degree and in high yields.

The use of promoters is not necessary.

The method of the invention makes possible an improvement in the yield (60–70%) and in the selectivity (80–90%).

The yields in the hydroformylation of higher epoxides are clearly greater than those which can be achieved with known methods.

Compared to the known method according to U.S. Pat. No. 3,463,819, the method of the invention has the advantage that a significantly smaller amount of catalyst is required. Thus, instead of 5 g catalyst for 3 g ethylene oxide only 400 mg catalyst is required for 2.2 g ethylene oxide.

No defined phosphinic oxide is used in the method according to U.S. Pat. No. 5,256,827.

The method of the invention, in which a defined phosphinic oxide compound is used, achieves distinctly greater yields although no promoters are used.

DETAILED DESCRIPTION OF THE PREFERRED EMBODIMENTS

EXAMPLES

Example 1

68.4 mg (0.2 mmol) dicobalt octacarbonyl, 321.6 mg (0.8 mmol) 1,2-bis(diphenylphosphino)methane monoxide (dppmO) and 20 ml toluene are placed into a 100 ml steel autoclave and washed with inert gas. The autoclave is equipped with a thermostatable dropping funnel with pressure compensation. 2.20 g (50 mmol) Liquid ethylene oxide and 1.00 g diethylene glycol methylether (standard for GC analytics) are placed into the dropping funnel cooled to 0° C. The autoclave is then closed and 100 bar synthesis gas (carbon monoxide-hydrogen mixture in a ratio of 1:1) is added. The reaction solution is then heated for a total of 4 h to 100° C. After 1 h, the ethylene oxide solution is added to the catalytic solution. After a reaction time of 3 h has elapsed, the autoclave is cooled down to 5° C., then the pressure is released and the autoclave is opened. The reaction solution is removed and the autoclave rinsed twice with 3 ml methanol each time. The combined organic phases are analyzed using gas chromatography. The results are shown in Table 1.

Examples 2–6

The procedure described in Example 1 is followed. Instead of 1,2-bis(diphenylphosphino) methane monoxide, o-diphenylphosphino methyl benzoate is used as catalyst. In addition, the ratio of ligand to cobalt and the reaction pressure are varied. The results are shown in Table 1.

TABLE 1

| Example | p (bar) | Ratio of ligand/cobalt | Yield 3-HPA (%) | Selectivity (%) |
|---|---|---|---|---|
| 1 | 100 | 2.0 | 65 | 90 |
| 2 | 150 | 0.25 | 28 | 66 |

TABLE 1-continued

| Example | p (bar) | Ratio of ligand/cobalt | Yield 3-HPA (%) | Selectivity (%) |
|---|---|---|---|---|
| 3 | 150 | 0.5 | 24 | 60 |
| 4 | 150 | 1.0 | 35 | 61 |
| 5 | 150 | 1.5 | 48 | 79 |
| 6 | 150 | 2.0 | 56 | 83 |

Example 7

The procedure used in Example 5 is followed. However, 2.9 g (50 mmol) propylene oxide are used as educt. The yield of 3-hydroxybutyraldehyde is 45%.

Examples 8–10

The procedure described in Example 4 is followed. However, 2.9 g (50 mmol) propylene oxide are used as educt. Instead of o-diphenylphosphino methyl benzoate, picolinic acid (Example 8), picolinic acid methyl ester (Example 9) and N,N-dimethyl glycine ethyl ester (Example 10) are used. The results are shown in Table 2.

TABLE 2

| Example | Selectivity to 3-hydroxyaldehydes/(%) | Yield of 3-hydroxybutyraldehyde (/%) |
|---|---|---|
| 8 | 65 | 36 |
| 9 | 57 | 34 |
| 10 | 50 | 34 |

Example 11

The procedure of Example 10 is followed; however, the reaction time is limited to 1 h. the yield of 3-hydroxybutyraldehyde is 51%.

What is claimed is:

1. A method of producing β-hydroxyaldehydes, comprising:

reacting 1,2-oxiranes with carbon monoxide and hydrogen in the presence of a cobalt transition metal compound, wherein said cobalt transition metal compound is modified with at least one phosphorus-oxygen ligand or nitrogen-oxygen ligand and is a catalyst;

wherein said phosphorus-oxygen ligand is selected from the group consisting of:

(I)

(II)

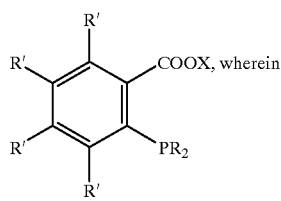

(III)

$R_1$, $R_2$, $R_3$ and $R_4$ individually represent alkyl, cycloalkyl or aryl groups of up to 30 carbon atoms, or —CH$_2$OH;

R' represents hydrogen, or an alkyl or cycloalkyl group having up to 30 carbon atoms;

Q represents an alkylidene bridge having 1–20 carbon atoms, a heteroatom, or a nitrogen-containing alkylidene;

X represents hydrogen, or an alkyl, cycloalkyl or aryl group; and the ratio of oxygen to phosphorus in ligands of formula (I) is greater than 0.5;

and wherein said nitrogen-oxygen ligand is selected from the group consisting of:

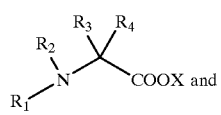

(IV)

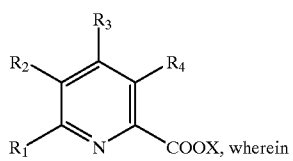

(V)

$R_1$, $R_2$, $R_3$ and $R_4$ individually represent hydrogen, or alkyl, cycloalkyl or aryl groups having up to 30 carbon atoms, optionally substituted with hydroxyl, amino or halogen groups;

$R_1$ and $R_2$ may optionally together form a cycloalkyl group having up to 20 carbon atoms;

$R_3$ and $R_4$ may optionally together form a cycloalkyl group having up to 20 carbon atoms; and X represents hydrogen, or an alkyl, cycloalkyl or aryl group.

2. The method according to claim 1, wherein said transition metal compound comprises a cobalt-carbonyl catalyst combined with a phosphinic oxide, wherein the ratio of oxygen to phosphorous in the phosphinic oxide is greater than 0.5 and less than or equal to 2.0.

3. The method according to claim 1, wherein the yield of β-hydroxyaldehydes is at least 60%.

4. The method according to claim 1, wherein the selectivity of β-hydroxyaldehydes is at least 80%.

5. The method according to claim 1, wherein the phosphorus-oxygen ligand is a compound of formula (I) in which Q represents an alkylidene bridge having 1–10 carbon atoms.

6. The method according to claim 1, wherein the ligand of formula (I) is selected from the group consisting of 1,2-bis(diphenylphosphino)methane monoxide and 1,2-bis(diphenylphosphino)ethane monoxide.

7. The method according to claim 1, wherein the phosphorus-oxygen ligand is a compound of formula (II) in which Q represents an alkylidene bridge having 1–10 carbon atoms, and in which $R_1$ and $R_2$ each contain up to 12 carbon atoms.

8. The method according to claim 1, wherein the ligand of formula (II) is selected from the group consisting of diphenylphosphino acetic acid and diphenylphosphino methyl acetate.

9. The method according to claim 1, wherein the phosphorus-oxygen ligand is a compound of formula (III) in which R' contains up to 12 carbon atoms.

10. The method according to claim 1, wherein the ligand of formula (III) is selected from the group consisting of o-diphenylphosphino benzoic acid and o-diphenylphosphino methyl benzoate.

11. The method according to claim 1, wherein the nitrogen-oxygen ligand is a compound of formula (IV) in which $R_1$, $R_2$, $R_3$ and $R_4$ each contain up to 12 carbon atoms.

12. The method according to claim 1, wherein the nitrogen-oxygen ligand is a compound of formula (IV) in which $R_1$ and $R_2$, or $R_3$ and $R_4$, or both, comprise a cycloalkyl group containing 4–7 carbon atoms.

13. The method according to claim 1, wherein the ligand of formula (IV) is selected from the group consisting of N,N-dimethylglycine and its ethyl ester.

14. The method according to claim 1, wherein the nitrogen-oxygen ligand is a compound of formula (V) in which $R_1$, $R_2$, $R_3$ and $R_4$ each contain up to 12 carbon atoms.

15. The method according to claim 1, wherein the nitrogen-oxygen ligand is a compound of formula (V) in which $R_1$ and $R_2$, or $R_3$ and $R_4$, or both, comprise a cycloalkyl group containing 4–7 carbon atoms.

16. The method according to claim 1, wherein the nitrogen-oxygen ligand is a compound of formula (V) in which X represents hydrogen or an ethyl group.

* * * * *